United States Patent [19]
Fuchs

[11] Patent Number: 5,945,534
[45] Date of Patent: Aug. 31, 1999

[54] PROCESS FOR THE PREPARATION OF OPTICALLY ACTIVE PIPERAZINE-2-CARBOXYLIC ACID DERIVATIVES

[75] Inventor: Rudolf Fuchs, Sion, Switzerland

[73] Assignee: Lonza AG, Gampel/Valais, Switzerland

[21] Appl. No.: 08/838,887

[22] Filed: Apr. 14, 1997

[30] Foreign Application Priority Data

Apr. 23, 1996 [CH] Switzerland ............................ 1028/96

[51] Int. Cl.$^6$ ...................... C07D 241/04; C07D 413/06
[52] U.S. Cl. ........................... 544/390; 544/388; 544/389; 544/121
[58] Field of Search ................................... 544/389, 390, 544/388, 121

[56] References Cited

U.S. PATENT DOCUMENTS

| | | | |
|---|---|---|---|
| 5,011,995 | 4/1991 | Pugin et al. | 564/302 |
| 5,491,238 | 2/1996 | Askin et al. | 544/388 |
| 5,612,484 | 3/1997 | Askin et al. | 544/388 |
| 5,618,939 | 4/1997 | Askin et al. | 544/390 |
| 5,663,341 | 9/1997 | Rossen et al. | 544/388 |
| 5,723,615 | 3/1998 | Rossen et al. | 544/388 |

FOREIGN PATENT DOCUMENTS

| | | |
|---|---|---|
| 0302021 | 1/1990 | European Pat. Off. . |
| 0541168 | 5/1993 | European Pat. Off. . |
| 0564406 | 10/1993 | European Pat. Off. . |
| 0612758 | 8/1994 | European Pat. Off. . |
| 0690955 | 11/1995 | European Pat. Off. . |
| 0744401 | 12/1995 | European Pat. Off. . |
| 2302690 | 1/1997 | United Kingdom . |
| WO 95/21162 | 8/1995 | WIPO . |

OTHER PUBLICATIONS

Felder et al., *Helv. Chim. Acta.*, (1960), 42, 888–896.
Hayashi et al., *J. Am. Chem. Soc.*, (1994), 116, 4221–4226.
Hayashi et al., *Bull. Chem. Soc. Jpn.*, (1980), 53, 1138–1151.
Landav et al., *J. Catalysis 157*, pp. 201–208 (1995).
Rossen et al, *Tetrahedron Letters 36*, pp. 6419–6422, Sep. 4, 1995.
Ornstein et al, *Bioorganic and Medicinal Chemistry Letters*, 3 pp. 43–48 (1993).

*Primary Examiner*—Emily Bernhardt
*Attorney, Agent, or Firm*—Fisher, Christen & Sabol

[57] ABSTRACT

Optically active piperazine-2-carboxylic acid derivatives of the general formula:

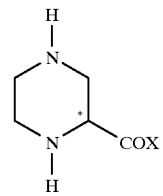

I in which X is alkoxy or a (substituted) amino group, are prepared by asymmetric hydrogenation of the corresponding pyrazinecarboxylic acid derivatives, catalyzed by optically active rhodium complexes. The compounds of the formula I are intermediates for the preparation of pharmaceutical active substances, for example, HIV protease inhibitors.

7 Claims, No Drawings

PROCESS FOR THE PREPARATION OF OPTICALLY ACTIVE PIPERAZINE-2-CARBOXYLIC ACID DERIVATIVES

BACKGROUND OF THE INVENTION

1. Field Of The Invention

The invention relates to a process for the preparation of optically active piperazine-2-carboxylic acid derivatives, especially esters and amides of (R)- or (S)-piperazine-2-carboxylic acid, which have the general formula:

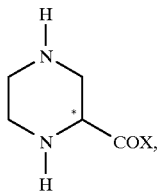

I in which X is a hydroxyl group, a $C_{1-6}$-alkoxy group or a group of the formula —$NR^1R^2$, in which in turn (i) $R^1$ and $R^2$ independently of one another are hydrogen, $C_{1-6}$-alkyl, $C_{3-6}$-cycloalkyl, aryl or an amino-protecting group, or (ii) $R^1$ and $R^2$, together with the nitrogen atom, form an optionally substituted 5-membered or 6-membered saturated heterocyclic ring, by asymmetric hydrogenation of the corresponding pyrazinecarboxylic acid derivatives. Compounds of this group are valuable intermediates, especially for the preparation of pharmaceutical active substances. Thus, for example, some known compounds, in which X is NH-t-Bu and which have the (S)-configuration, are structural units for HIV protease inhibitors (European Published Patent Application No. 0,541, 168).

2. Background Art

Hitherto known syntheses of compounds of the formula I are based on the parent compound (X is OH), which can be obtained in optically active form by conventional resolution of the racemate [E. Felder et al., Helv. Chim. Acta, (1960), 43, 888–896]. First, the ring nitrogen atoms are protected and then the free carboxyl group is converted to the amide. At best the process is suitable for the laboratory scale and requires the use of expensive reagents.

BROAD DESCRIPTION OF THE INVENTION

The main object of the invention is to provide a synthesis process of the optically active piperazine-2-carboxylic acid derivatives of the general formula I which can be carried out on the industrial scale and which does not involve resolution of the racemate. Other objects and advantages of the invention are set out herein or are obvious herefrom to one skilled in the art.

The objects and advantages of the invention are achieved by the process of the invention.

The invention involves a process for the preparation of optically active piperazine-2-carboxylic acid derivatives of the general formula:

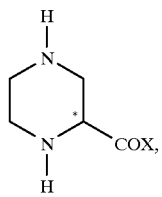

I in which X is a hydroxyl group, a $C_{1-6}$-alkoxy group or a group of the formula —$NR^1R^2$, in which in turn (i) $R^1$ and $R^2$ independently of one another are hydrogen, $C_{1-6}$-alkyl, $C_{3-6}$-cycloalkyl, aryl or an amino-protecting group, or (ii) $R^1$ and $R^2$, together with the nitrogen atom, form an optionally substituted 5-membered or 6-membered saturated heterocyclic ring. The invention process includes asymmetrically hydrogenating a corresponding pyrazinecarboxylic acid derivative of the general formula:

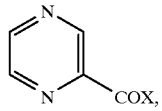

II in which X is as defined above, in the presence of a catalytically active, optically active rhodium complex.

DETAILED DESCRIPTION OF THE INVENTION

Herein, $C_{1-n}$-alkyl is to be understood as meaning linear or branched primary, secondary or tertiary alkyl groups having 1 to n carbon atoms; thus, for example, $C_{1-6}$-alkyl is to be understood as meaning groups such as methyl, ethyl, propyl, butyl, pentyl, hexyl, isopropyl, isobutyl, tert-butyl, isopentyl and neopentyl. Correspondingly $C_{1-n}$-alkoxy is to be understood as meaning groups made up of $C_{1-n}$-alkyl and oxygen. Aryl is to be understood as meaning especially groups such as phenyl or substituted phenyl. $C_{3-6}$-cycloalkyl is to be understood as meaning cyclopropyl, cyclobutyl, cyclopentyl or cyclohexyl. Amino-protecting groups are to be understood as meaning the protecting groups conventionally used in peptide chemistry, for example, benzyloxycarbonyl ("Z") or tert-butoxycarbonyl ("Boc"). The expression "saturated heterocyclic ring" also includes rings having several heteroatoms, which may be different, an example being morpholine.

It has been found that the pyrazinecarboxylic acid derivatives corresponding to the target compounds, of the general formula:

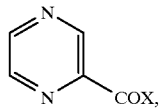

II in which X is as defined above, can be asymmetrically hydrogenated to the target compounds with hydrogen in the presence of catalytically active, optically active rhodium complexes.

The pyrazinecarboxylic acid derivatives used are preferably the amides, in which X is a group of the formula —$NR^1R^2$ and $R^1$ and $R^2$ are as defined above.

Particularly preferred amides are those in which $R^1$ is hydrogen and $R^2$ is a $C_{1-6}$-alkyl group, especially a tert-butyl group.

The pyrazinecarboxylic acid derivatives II are known compounds or are obtainable by known methods from the commercially available compounds pyrazinecarboxylic acid, pyrazinecarboxamide and pyrazinecarbonitrile.

The catalytically active, optically active rhodium complex used is preferably a rhodium complex formed by reacting an Rh(I) complex with an optically active metallocenylphosphine.

The optically active metallocenylphosphines used are preferably compounds of the general formula:

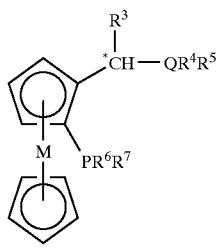

III in which M is iron (II) or ruthenium (II), Q is nitrogen or phosphorus, $R^3$ is a $C_{1-4}$-alkyl group and $R^4$ to $R^7$ independently of one another are $C_{1-8}$-alkyl, $C_{5-8}$-cycloalkyl, phenyl or substituted phenyl.

Particularly preferred metallocenylphosphines are those in which M is iron (II), i.e., the ferrocenylphosphines.

Other particularly preferred metallocenylphosphines are those in which Q is phosphorus, i.e., metallocenyldiphosphines.

Other particularly preferred metallocenylphosphines are those in which $R^3$ is methyl and $R^4$ and $R^5$ are identical and are tert-butyl or cyclohexyl. These last-mentioned metallocenylphosphines include, for example, 1-[1-(di-tert-butylphosphino)ethyl]-2-(diphenylphosphino)ferrocene and 1-[1-(dicyclohexylphosphino)ethyl]-2-(diphenylphosphino) ferrocene. The preparation of these compounds is described in U.S. Pat. No. 5,466,844.

Other optically active metallocenylphosphines are described, for example, in T. Hayashi et al., *J. Am. Chem. Soc.*, (1994), 116, 4221–4226, in European Published Patent Application No. 0,612,758 and in T. Hayashi et al, *Bull. Chem. Soc. Jpn.*, (1980), 53, 1138–1151.

Neutral dinuclear complexes of the general formula:

[Rh(L)A]$_2$     IV are preferably used as Rh(I) complexes which, together with the optically active metallocenylphosphines, form the catalytically active, optically active rhodium complexes. In formula IV, L is a $C_{4-12}$-diene or two $C_{2-12}$-alkene molecules, and A is chlorine, bromine or iodine, preferably chlorine or bromine.

Other preferred Rh(I) complexes are those of the general formula:

[Rh(L)$_2$]$^+$B$^-$     V in which L is as defined above and B$^-$ is the anion of an oxo acid or complex acid. Anions of oxo acids are to be understood as meaning, for example, anions such as $ClO_4^-$, $SO_3F^-$, $CH_3SO_3^-$ or $CF_3SO_3^-$, and anions of complex acids are to be understood as meaning, for example, anions such as $BF_4^-$, $PF_6^-$, $AsF_6^-$, $SbF_6^-$ or $SbCl_6^-$.

Particularly preferred ligands L in the Rh(I) complexes IV and V are dienes, especially norbornadiene and 1,5-cyclooctadiene. These complexes are known, for example, from European Published Patent Application No. 0,302,021 or U.S. Pat. No. 5,011,995.

The asymmetric hydrogenation of the pyrazinecarboxylic acid derivatives II is advantageously carried out at a temperature of 20° to 200° C. and a hydrogen pressure of 1 to 200 bar. The molar ratio of catalyst to educt is advantageously 1:5 to 1:2000, preferably 1:20 to 1:100.

Examples of suitable solvents for the asymmetric hydrogenation are water, lower alcohols such as methanol, aromatic hydrocarbons such as toluene, ketones such as acetone, or carboxylic acid esters such as ethyl acetate.

The following examples illustrate how the process according to the invention is carried out and how the compounds according to the invention are prepared, without thereby implying any limitations.

EXAMPLE 1

Methyl pyrazinecarboxylate 106.6 g of thionyl chloride was added dropwise over 1 hour at 4° to 6° C. to 1200 ml of methanol under argon. 100.1 g of pyrazinecarboxylic acid was added at 9° C. and the mixture was heated for 2 hours at 61° C., with the acid passing completely into solution. After cooling to room temperature, a solution of 145 g of sodium hydrogen carbonate in 1.4 l of water was added slowly. The methanol was distilled off on a rotary evaporator at 50 to 120 mbar and a bath temperature of 45° C., and the residue was extracted three times with dichloromethane (400 ml, 100 ml, 100 ml). Concentration of the organic phase provided 83.15 g of crude product, which was recrystallized from ca. 250 g of diisopropyl ether. The yield of the title compound was 70.6 g, plus 10.28 g from the mother liquor (total: 72.5 percent). Other data concerning the title compound was:

$^1$H NMR (CDCl$_3$, 400 MHz): δ 4.08 (s, 3H); 8.75 (d, J=0.5 Hz, 1H); 8.80 (d, J=0.5 Hz, 1H); 9.30 (s, 1H).

EXAMPLE 2

Tert-butyl pyrazinecarboxylate A mixture of 20 ml of N,N-dimethylformamide and 50 ml of acetonitrile was cooled to −20° C. and a solution of 11.16 g (80 mmol) of oxalyl chloride in 10 ml of acetonitrile was added dropwise over 20 minutes at this temperature under argon. 10 g (80 mmol) of pyrazinecarboxylic acid (Fluka) was then added in portions at −20° C. The mixture was stirred for a further 20 minutes at this temperature and 20 ml (212 mmol) of tert-butyl alcohol in 20 ml of pyridine was added dropwise. The cooling means were removed and the reaction mixture was left to stand overnight at room temperature. The mixture was then shaken with 300 ml of dichloromethane and 300 ml of 20 percent aqueous potassium hydrogen carbonate solution. The phases were separated and the aqueous phase was re-extracted with dichloromethane. The solvent was distilled from the combined organic phases to give the title compound in the form of an oil. The yield of the title compound was 9.02 g (62 percent), content (GC): 99 percent.

EXAMPLE 3

Pyrazinecarboxylic acid tert-butylamide 575 g (5.75 mmol) of sulfuric acid was added dropwise to 900 ml of acetic acid over 35 minutes at 20° C. (cooling), followed by 200.1 g (1.9 mol) of cyanopyrazine over 20 minutes. 142.4 g (2.54 mol) of isobutene was then introduced over 3.5 hours, the temperature being kept below 25° C. by appropriate cooling. The mixture was subsequently stirred for a further 2 hours at room temperature and then poured into 1.8 l of ice-water. The mixture was brought to pH 3.5 by the slow addition of 1527 g of 30 percent sodium hydroxide solution and then extracted continuously for 4 hours with 2.5 l of hot methylcyclohexane in a liquid-liquid extractor. The extract was cooled to 4° C., with stirring, and the product which had crystallized out was filtered off and dried under vacuum. The yield of the title compound was 246 g, content (titration): 99.6 percent. Concentration of the mother liquor gave a further 22.5 g of the title compound with a content of 99.0 percent. The total yield of the title compound was 268.5 g (78 percent).

EXAMPLE 4
(S)-Piperazine-2-carboxylic acid tert-butylamide 0.5 g (2.7 mmol) of pyrazinecarboxylic acid tert-butylamide (prepared according to Example 3), 26.9 mg (58 μmol) of bicyclo[2.2.1]hepta-2,5-dienerhodium(I) chloride dimer and 72 mg (121 μmol) of 1-[1 (R)-(dicyclohexylphosphino)ethyl]-2(S)-(diphenylphosphino) ferrocene were placed in an autoclave under argon. After the addition of 10 ml of degassed methanol, the autoclave was flushed three times with argon and twice with hydrogen. A hydrogen pressure of 50 bar was then applied. Hydrogenation was carried out at 70° C. for 20 hours. The autoclave was depressurized and flushed with nitrogen. The solvent was completely distilled off. The yield of the title compound was 0.50 g. A conversion of 80 percent was determined by NMR. The enantiomeric excess (ee) was 77.6 percent according to GC analysis.

EXAMPLE 5
(S)-Piperazine-2-carboxylic acid tert-butylamide

The procedure was as described in Example 4 except that only 25.3 mg (54 μmol) of bicyclo[2.2.1]hepta-2,5-dienerhodium(I) chloride dimer was used and the 1-[1(R)-(dicyclohexylphosphino)ethyl]-2(S)-(diphenylphosphino) ferrocene was replaced with 61.5 mg (113.3 μmol) of 1-[1 (R)-(di-tert-butylphosphino)ethyl]-2(S)-(diphenylphosphino)ferrocene. A conversion of 97 percent was determined by NMR. The enantiomeric excess (ee) was 57.6 percent according to GC analysis.

EXAMPLE 6
(S)-Piperazine-2-carboxylic acid tert-butylamide

Analogously to Example 4, 5 g (27 mmol) of pyrazinecarboxylic acid tert-butylamide, 127 mg (0.27 mmol) of bicyclo[2.2.1]hepta-2,5-dienerhodium(I) chloride dimer and 353 mg (0.594 mmol) of 1-[1 (R)-(dicyclohexylphosphino) ethyl]-2(S)-(diphenylphosphino)ferrocene were hydrogenated for 20 hours in 70 ml of methanol at 100° C. and 50 bar. A conversion of 85 percent was determined by NMR. The enantiomeric excess (ee) was 49 percent according to GC analysis.

EXAMPLE 7
Tert-butyl (S)-piperazine-2-carboxylate

Analogously to Example 4, 0.52 g (2.85 mmol) of tert-butyl pyrazinecarboxylate (prepared according to Example 2), 25.3 mg (54 μmol) of bicyclo[2.2.1 ]hepta-2,5-dienerhodium(I) chloride dimer and 61.5 mg (113.3 μmol) of 1-[1(R)-(di-tert-butylphosphino)ethyl]-2(S)-(diphenylphosphino)ferrocene were hydrogenated for 20 hours in 10 ml of methanol at 70° C. and 50 bar. A conversion of 67 percent was determined by NMR. The ee value was determined by hydrolyzing the ester (see Example 8).

EXAMPLE 8
(S)-Piperazine-2-carboxylic acid dihydrochloride

The crude tert-butyl (S)-piperazine-2-carboxylate from Example 7 was stirred in 2.9 g of water and 2.1 g (18.4 mmol) of 32 percent hydrochloric acid for 20 minutes at 100° C. The mixture was cooled to 0° C. and stirred for a further 1 hour. The hydrochloride which had precipitated out was filtered off and washed with 10 ml of dichloromethane. The yield of the title compound was 0.24 g (41 percent, based on tert-butyl pyrazinecarboxylate). The ee value was 77.6 percent.

EXAMPLE 9
Methyl (S)-piperazine-2-carboxylate

Analogously to Example 4, 0.52 g (3.5 mmol) of methyl pyrazinecarboxylate (prepared according to Example 1), 33.6 mg (72.8 μmol) of bicyclo[2.2.1]hepta-2,5-dienerhodium(I) chloride dimer and 92.9 mg (171 μmol) of 1-[1(R)-(di-tert-butylphosphino)ethyl]-2(S)-(diphenylphosphino)ferrocene were hydrogenated for 20 hours in 10 ml of methanol at 70° C. and 50 bar. A conversion of 85 percent was determined by NMR. The ee value was determined by hydrolyzing the ester according to Example 8. The ee value was 3.6 percent.

What is claimed is:

1. A process for the preparation of an optically active piperazine-2-carboxylic acid derivative of the formula:

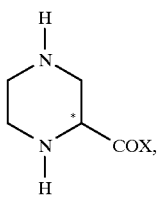

I wherein X is a hydroxyl group, a $C_{1-6}$-alkoxy group or a group of the formula $-NR^1R^2$, in which in turn
(i) $R^1$ and $R^2$ independently of one another are hydrogen, $C_{1-6}$-alkyl, $C_{3-6}$-cycloalkyl, aryl or an amino-protecting group, or
(ii) $R^1$ and $R^2$, together with the nitrogen atom, form a morpholino ring, comprising asymmetrically hydrogenating a corresponding pyrazinecarboxylic acid derivative of the formula:

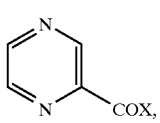

II wherein X is as defined above, in the presence of a catalytically active, optically active rhodium complex, comprising a complex formed from (a) an Rh(I) complex and (b) an optically active metallocenylphosphine, the Rh(I) complex (a) is a neutral complex of the formula:

IV wherein L is a $C_{4-12}$-diene or two $C_{2-12}$-alkene molecules and A is chlorine, bromine or iodine, or is a cationic complex of the formula:

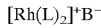

V wherein L is a $C_{4-12}$-diene or two $C_{2-12}$-alkene molecules and $B^{31}$ is the anion of an oxo acid or complex acid, and the optically active metallocenylphosphine (b) used is a compound of the formula:

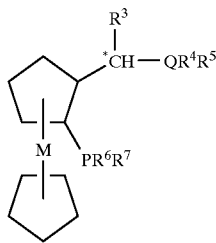
III wherein M is iron(II), Q is phosphorus, $R^3$ is a $C_{1-4}$-alkyl group and $R^4$ to $R^7$ independently of one another are $C_{1-8}$-alkyl, $C_{5-8}$-cycloalkyl or phenyl.

2. The process according to claim 1, wherein the pyrazinecarboxylic acid derivative II used is a compound in which X is a group of the formula $—NR^1R^2$, $R^1$ and $R^2$ being as defined above.

3. The process according to claim 2, wherein $R^1$ is hydrogen and $R^2$ is a $C_{1-6}$-alkyl group.

4. The process according to claim 3, wherein $R^2$ is a tert-butyl group.

5. The process according to claim 1, wherein L in the neutral complex of the formula IV is norbomadiene or 1,5-cyclooctadiene.

6. The process according to claim 1, wherein L in the cationic complex of the formula V is norbomadiene or 1,5-cyclooctadiene.

7. The process according to claim 1, wherein, in the optically active metallocenylphosphine of formula III, $R^3$ is methyl, and $R^4$ and $R^5$ are identical and are tert-butyl or cyclohexyl.

* * * * *